US011559453B2

(12) United States Patent
Stokesbary

(10) Patent No.: US 11,559,453 B2
(45) **Date of Patent: *Jan. 24, 2023**

(54) NON-RESTRAINING COLLAR

(71) Applicant: Carla Stokesbary, Cincinnati, OH (US)

(72) Inventor: Carla Stokesbary, Cincinnati, OH (US)

( * ) Notice: Subject to any disclaimer, the term of this patent is extended or adjusted under 35 U.S.C. 154(b) by 155 days.

This patent is subject to a terminal disclaimer.

(21) Appl. No.: 17/188,465

(22) Filed: Mar. 1, 2021

(65) Prior Publication Data

US 2021/0177682 A1 Jun. 17, 2021

Related U.S. Application Data

(63) Continuation of application No. 15/884,080, filed on Jan. 30, 2018, now Pat. No. 10,932,971.

(60) Provisional application No. 62/451,975, filed on Jan. 30, 2017.

(51) Int. Cl.

| | |
|---|---|
| ***A61F 5/055*** | (2006.01) |
| ***A61G 7/07*** | (2006.01) |
| ***A47G 9/10*** | (2006.01) |
| ***A47C 7/38*** | (2006.01) |
| *A61G 5/12* | (2006.01) |
| *A61G 15/12* | (2006.01) |
| *A61G 13/12* | (2006.01) |

(52) U.S. Cl.

CPC .............. *A61G 7/072* (2013.01); *A47C 7/383* (2013.01); *A47G 9/1081* (2013.01); *A47G 2009/1018* (2013.01); *A61G 5/121* (2016.11); *A61G 13/121* (2013.01); *A61G 15/125* (2013.01)

(58) Field of Classification Search

CPC ........ A61F 5/05; A61F 5/055; A61F 5/05883; A61F 5/37; A47C 7/383; A61G 5/121; A61G 7/072; A61G 15/125; A47G 9/1081; A47G 2009/1018

See application file for complete search history.

(56) References Cited

U.S. PATENT DOCUMENTS

| | | | | |
|---|---|---|---|---|
| 2,088,207 | A | 7/1937 | Henry | |
| 2,284,058 | A | 5/1942 | Henry et al. | |
| 2,774,601 | A | 12/1956 | White | |
| 3,374,785 | A | 3/1968 | Gaylord, Jr. | |
| 3,964,474 | A | 6/1976 | Fox | |
| 4,617,691 | A | 10/1986 | Monti et al. | |
| 6,219,865 | B1 | 4/2001 | Stokesbary | |
| 7,185,378 | B2 | 3/2007 | Smith | |
| 8,733,362 | B2 * | 5/2014 | Krook | A61F 5/56 601/39 |
| 9,032,570 | B1 | 5/2015 | Benami | |

* cited by examiner

*Primary Examiner* — Camtu T Nguyen

(74) *Attorney, Agent, or Firm* — Ulmer & Berne LLP

(57) ABSTRACT

A non-restraining collar can include a unitary pillow having extending from a collar body first and second collar straps that extend opposite one another and terminate in respective distal ends separated by a space having a first distance in a relaxed state. The non-restraining collar can also include an elastically deformable spring member embedded in the unitary pillow, the elastically deformable spring member having portions extending into both of the first and second collar straps. The elastically deformable spring member can be deformed such that the first distance is increased to a second distance.

20 Claims, 6 Drawing Sheets

NON-RESTRAINING COLLAR

REFERENCE TO RELATED APPLICATION

The present application is a continuation of U.S. patent application Ser. No. 15/884,080, filed Jan. 30, 2018, which claims the priority benefit of U.S. Provisional Patent Application Ser. No. 62/451,975, filed Jan. 30, 2017, and hereby incorporates the same applications by reference in their entireties.

TECHNICAL FIELD

Embodiments of the technology relate, in general, to devices useful for those suffering from conditions of neck myopathy including isolated neck extensor myopathy, also known as drop head syndrome.

BACKGROUND

Many people, particularly elderly people suffer from a condition known as isolated neck extensor myopathy, also known as drop head syndrome. This condition often has a negative social impact, as it can result in the loss of self-esteem and dignity for the person suffering there from it. Drop head syndrome also can create breathing and swallowing difficulties (dysphagia) for the person suffering from this condition, and this, of course, can lead to an array of other health problems.

This condition also impacts caregivers, as they must invest more attention and time to the patient having this condition. Often a caregiver is required to coax a patient into lifting his or her head, or the caregiver must physically lift the head to feed a patient, often needing to do this with every bite of food.

Use of pillows or other items to hold the head up can be problematic with respect to comfort and safety. In particular, such items can be a restraint, meaning that the person using it cannot independently remove it without difficulty.

DETAILED DESCRIPTION

Figure 1:
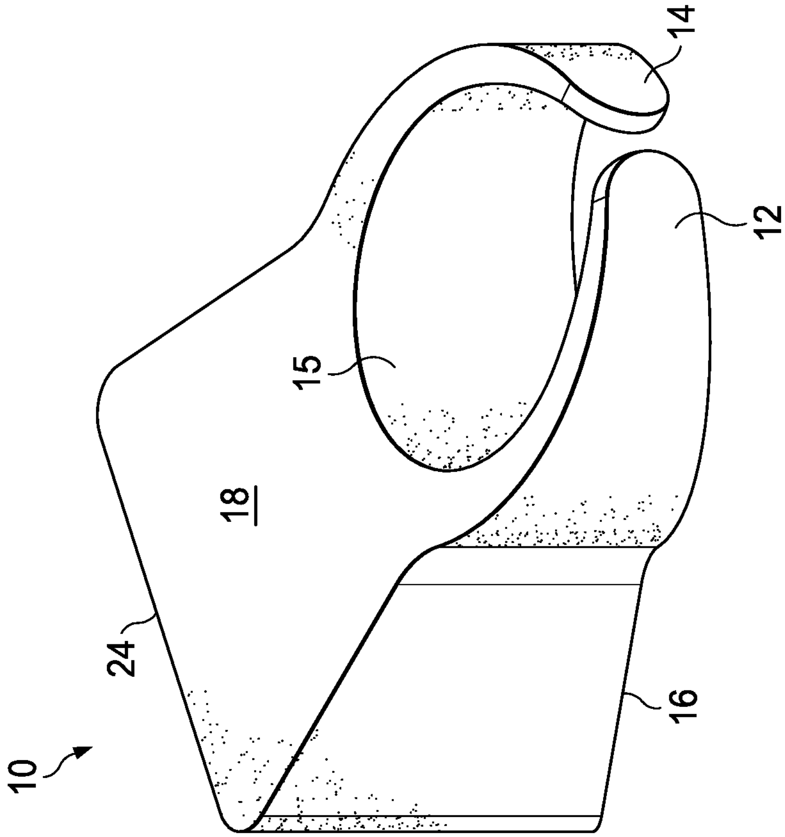
FIG. 1 is a perspective view of a neck collar according to one embodiment.

Certain embodiments are hereinafter described in detail in connection with the views and examples of FIGS. 1-11, wherein like numbers refer to like elements throughout the views.

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific FIG. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Addressing the problems associated with isolated neck extensor myopathy can be achieved by use of embodiments of a neck collar disclosed here in. The neck collar embodiments disclosed herein offer advantages in comfort, safety, and cost.

Figure 11:
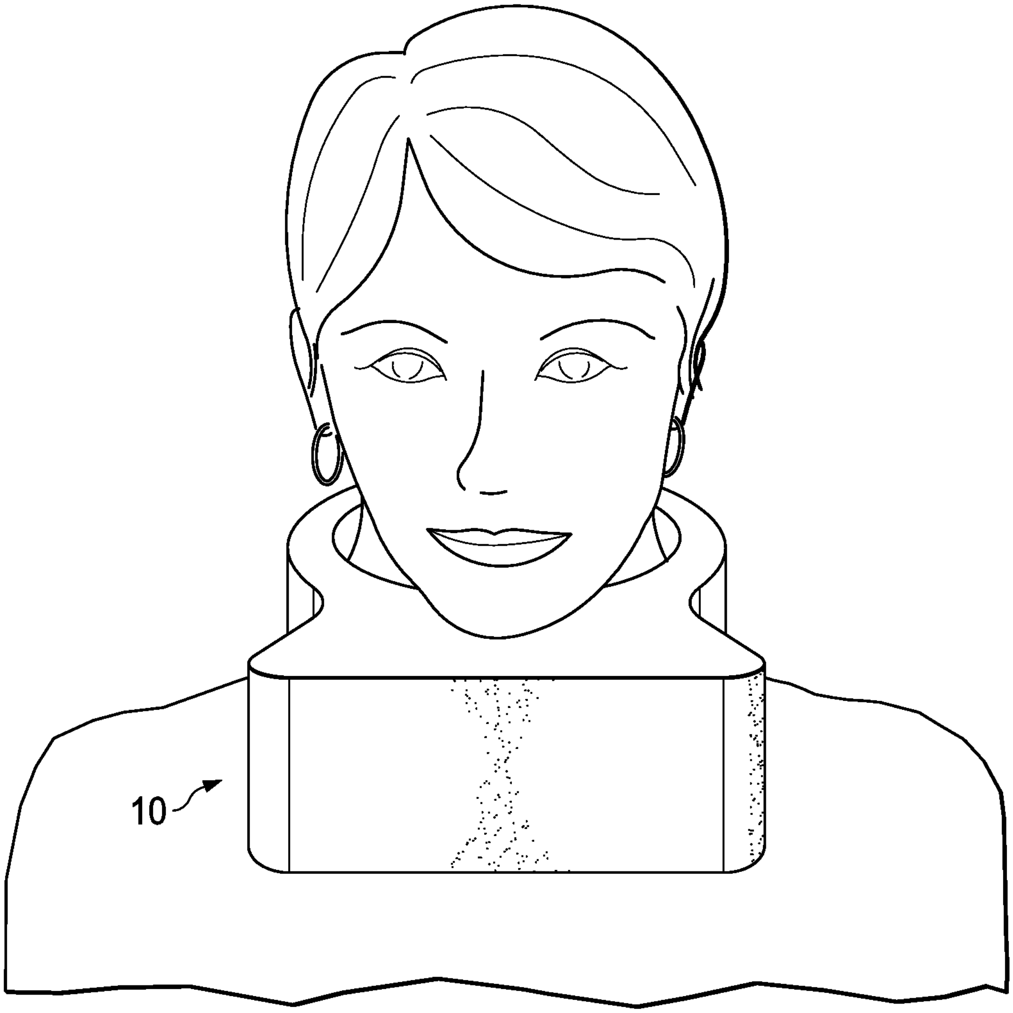
FIG. 11 is a front view of a neck collar according to one embodiment in use by a person.

Referring to FIG. 1, there is shown an example embodiment of a neck collar 10 in the form of a soft pillow for providing neck support to a person who may not be able to hold his or her chin up. The neck collar is intended to be worn about the neck of a user and includes first collar strap 12 and second collar strap 14 positioned opposite first collar strap 12, the collar straps configured for encircling the neck of the user sufficiently to secure the neck collar 10 to the wearer so that it can fit comfortably and will not fall off if the wearer alters his or her position. The first and second collar straps each extend a length from a side of the pillow and terminate in first and second distal ends, respectively. Together, the first and second collar straps define a neck opening 15 having sufficient size to comfortably fit on the neck of a wearer. Collar straps 12, 14 can be relatively soft, and can be, as discussed below, injection foam molded in a unitary structure with the neck collar 10. The neck opening 15 can be provided in different sizes so that the wearer can choose the most comfortable. The neck collar 10 has an upper surface 18 which, in use, is a surface on which the chin of a user can rest. The neck collar 10 also has a lower surface 16, which, in use, is intended to rest on the clavicles of the user. Thus, when in use, as depicted in FIG. 11, the neck collar serves to hold the chin and head of a user in a relatively upright, comfortable position.

Figure 6:
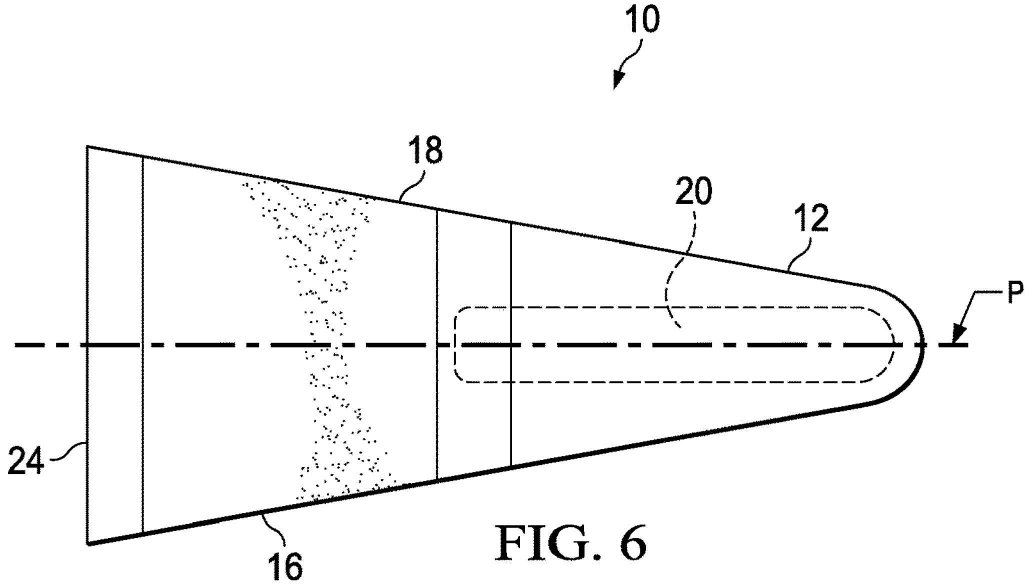
FIG. 6 is side view of a neck collar according to one embodiment.
Figure 7:
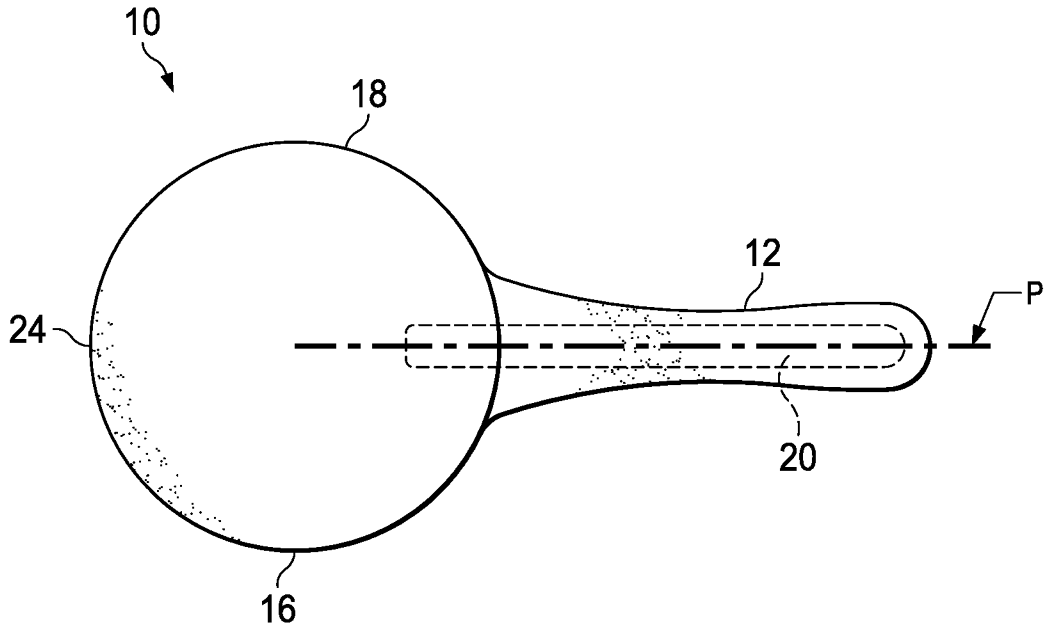
FIG. 7 is side view of a neck collar according to one embodiment.

In an example embodiment, the collar straps 12, 14 are disposed substantially in a plane P, as shown in FIGS. 6 and 7, and can be generally symmetric about plane P. First and second collar straps 12, 14 can be resiliently flexible such that they can be spread apart wide enough to accommodate placement on the neck of a user, and then return to a relaxed position, as shown in FIG. 1, thereby encircling the neck of the user. When encircling the neck of the user, the neck collar 10 can remain in place as a chin and head support without any restraining parts that would prevent the user from relatively easily removing the neck collar. For example, a user can remove the neck collar 10 by merely pulling at it such that the resiliently flexible collar straps 12, 14 spread sufficiently such that the neck collar 10 can be removed from the neck of the user. In this manner, the neck collar 10 can be easily placed on the neck of the user, and likewise can be easily removed from the neck of a user, including by the user, without the need to unfasten any fasteners such as hook and loop fasteners, buckles, hooks, buttons or the like. This feature of the neck collar can be important because many jurisdictions require that a patient or resident be free from physical restraint, even for items that are imposed for convenience. Again, as discussed, the neck collar 10 disclosed herein is not a restraint; the user can easily put it on and remove it without out need to unstrap, unbuckle, tear apart, or otherwise manipulate a closure mechanism.

Figure 2:
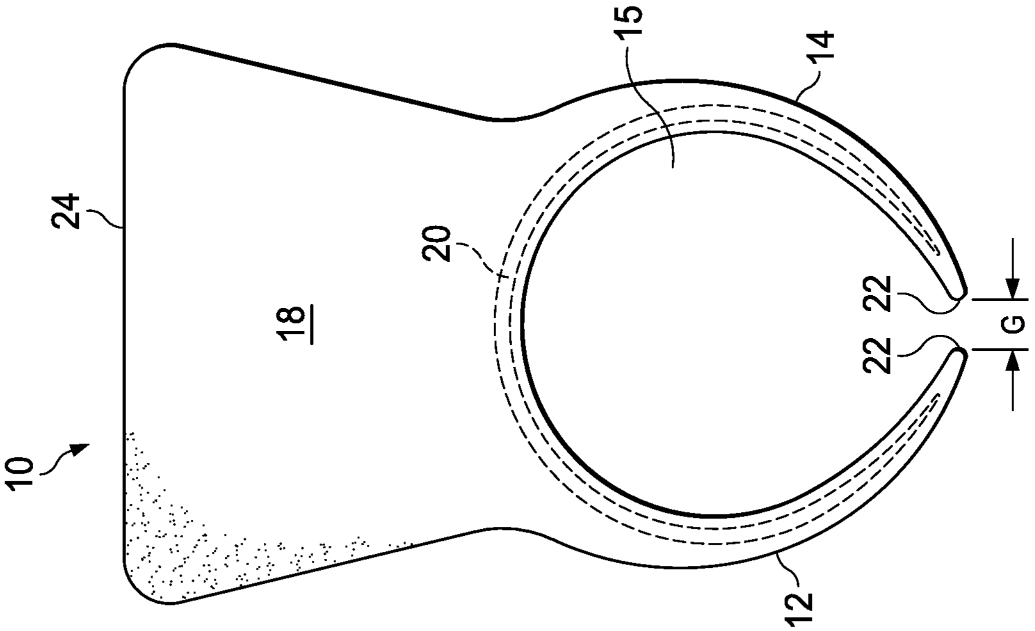
FIG. 2 is top view of a neck collar according to one embodiment.

Referring now to FIG. 2, there is a top view of an example of a neck collar 10. As shown, the collar straps 12 and 14 can be in a shape that naturally follows the contours of the neck of a person. That is, the collar straps 12 and 14, together with a portion of the neck collar 10 can define a generally circular shaped neck opening 15, but the shape need not be exactly circular. The collar straps can, when in a relaxed state, have a space, referred to as gap G, that spans a first distance between the distal ends 22 thereof, as shown in FIG. 2. The gap G can have a length dimension ranging from 0 inches to about 5 inches, and, in some embodiments the distal ends 22 of collar straps 12 and 14 can overlap when in a relaxed state. When collar straps 12 and 14 are in a relaxed state it can be important that the neck opening 16 be sufficiently sized for the neck of a user, and that neck collar 10 not feel uncomfortably tight on the neck of a user. Likewise, gap G can be wide enough that ease-of-use is facilitated, but not so wide that the neck collar 10 fails to remain on the neck of the user during use.

Continuing in reference to FIG. 2, the spring resiliency of the collar straps 12 and 14 can be provided by an elastically deformable spring member 20 that, when in a relaxed state, takes the desired shape for the neck opening 15 of the neck collar 10. As shown additionally in the side view of FIG. 6, the elastically deformable spring member 20 can be a generally constant thickness, constant width band of springy material, such as metal or plastic. In an embodiment the elastically deformable elastically deformable spring member 20 is relatively lightweight, such as would be the case with thin metal or plastic. Elastically deformable spring member 20 can be a unitary member having a relaxed shape of a band, as shown, but which can be temporarily deformed sufficiently that gap G is enlarged to fit past the neck of a wearer. That is, in practice, collar straps 12, 14 can be manipulated for placement or removal on the neck of a user by deforming the elastically deformable spring member 20 such the distance between distal ends 22 of first and second collar straps increases sufficiently to clear the neck of a user. Once placed on the neck of a user, the elastically deformable spring member 20 can return to, or close to, its relaxed state and remain on the neck of the user without the use of, and in the absence of, any fastening members, such as hook and loop fasteners, buckles, hooks buttons, or the like, that could constrain removal by the user.

Elastically deformable spring member 20 can be a unitary member as shown in FIG. 2, but can also be two or more members that cooperate functionally to provide for an elastically deformable spring function to collar straps 12 and 14. For example, as shown in FIG. 3, two elastically deformable spring members, 20A and 20B can be embedded in neck collar 10 by the methods described below, and provide the function of rendering collar straps 12 and 14 resiliently openable for positioning the neck collar about the neck of a user, and having spring memory to return to a relaxed state in which the distance of gap G is sufficiently small to prevent the neck collar 10 from inadvertently coming off the neck of a user during use.

Figure 4:
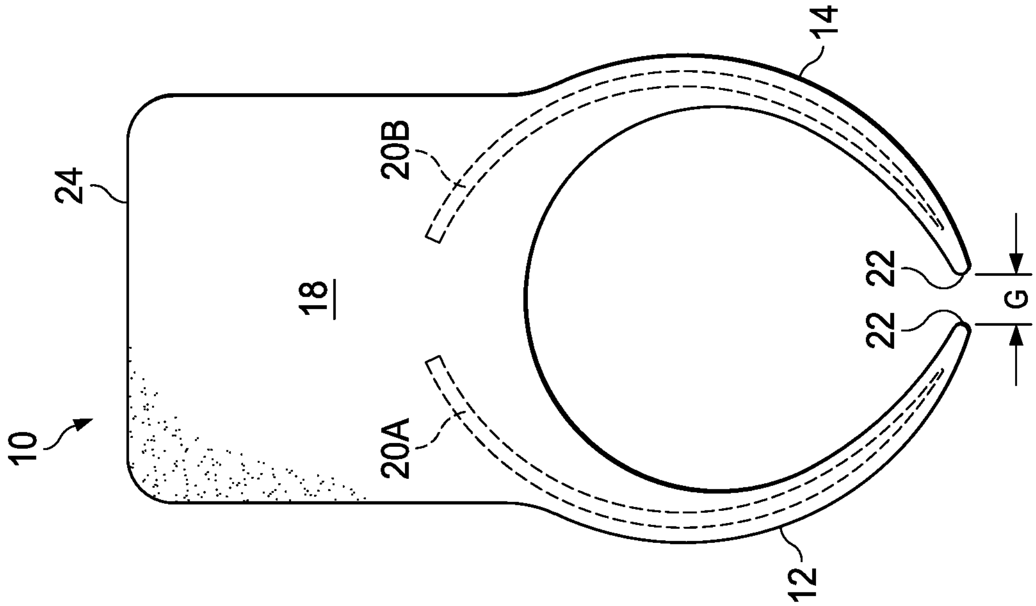
FIG. 4 is top view of a neck collar according to one embodiment.
Figure 3:
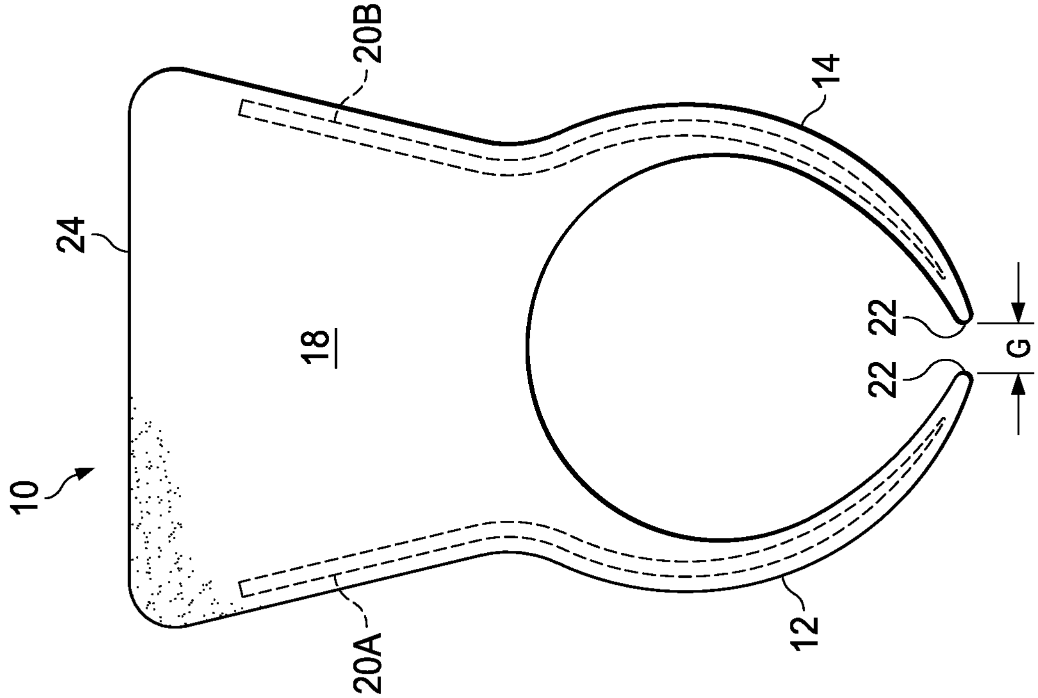
FIG. 3 is top view of a neck collar according to one embodiment.

The elastically deformable spring members 20A and 20B of FIG. 3 are shown extending outwardly to near the outer side surfaces of neck collar 10. As can be understood, when the collar straps 12, 14 are urged outwardly, such that gap G is enlarged, the portions of elastically deformable spring members 20A and 20B embedded in the pillow body portion of neck collar 10 can be restrained from relative movement by the internal pillow body in which they are embedded, thus providing for the spring elastically deformable return of the collar straps 12, 14 once the outward urge of the collar straps is removed. Likewise, as shown in FIG. 4, the elastically deformable spring members 20A and 20B can be embedded more centrally into the internal pillow body, with the principle of operation being the same as described above. Also depicted in FIG. 4, neck collar 10 need not be limited to a wedge shape as viewed from above but can have any shape sufficient to contact and hold the chin of a user up when resting on the chest or clavicles of the user.

Figure 5:
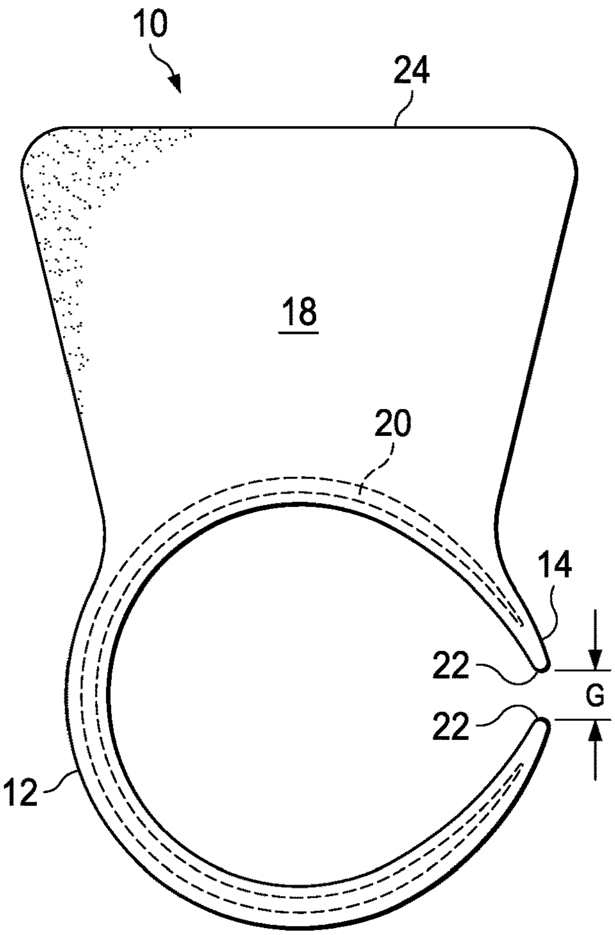
FIG. 5 is top view of a neck collar according to one embodiment.

Referring now to FIG. 5, there is shown another embodiment of neck collar 10. As shown, rather than the distal ends 22 of collar straps 12, 14 being oriented such that gap G resides at the back of a user during use, neck collar 10 can be configured such that gap G resides in a different position with respect to the neck of a user. As shown, for example, gap G can be disposed at a different position, such that in use neck collar 10 can be placed on the neck of a user from the side. In general, neck collar 10 can have generally symmetric collar straps 12, 14 in which a gap G resides centrally directly opposite the front surface 24 of neck collar 10, or asymmetric collar straps 12, 14, in which gap G resides off center and to one side of neck collar 10. In other words, viewing from the top, as in FIGS. 2-5, the opening separating distal ends 22 of collar straps 12, 14 can reside at a “six o’clock” position as shown in FIG. 2, or in another position, such as the “two-o’clock” position shown in FIG. 5. In an embodiment, one of either first collar strap 12 or second collar strap 14 can extend substantially the entire length sufficient to encircle the neck of a user, thus rendering the other collar strap unnecessary.

Referring to FIG. 6, there is shown a representative side view of a neck collar 10, showing in one embodiment where elastically deformable spring member 20 can be placed therein. As shown in FIG. 6, neck collar 10 can have a generally wedge shape in side profile but is not limited to such as shape. As shown in FIG. 3, the large end of the wedge shape is to the left and terminates at a front surface 24. The narrow end of the wedge shape is in FIG. 3 on the right and terminates at the collar straps 12 and 14. As shown in FIG. 6, elastically deformable spring member 20 can be embedded into neck collar 10 and extend into collar straps 12 and 14.

Figure 8:
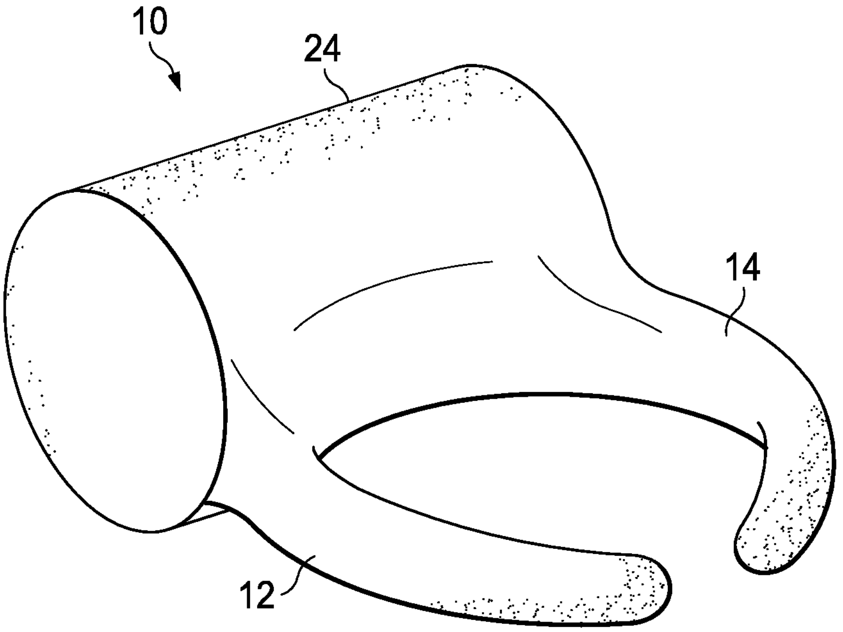
FIG. 8 is a perspective view of a neck collar according to one embodiment.

Another representative embodiment of a neck collar 10 is shown in FIGS. 7 and 8. In the side view shown in FIG. 7 and the perspective view shown in FIG. 8, neck collar 10 can be a substantially rounded, generally cylindrically shaped pillow having collar straps in which is embedded a elastically deformable spring member 20, as described herein.

Figure 9:
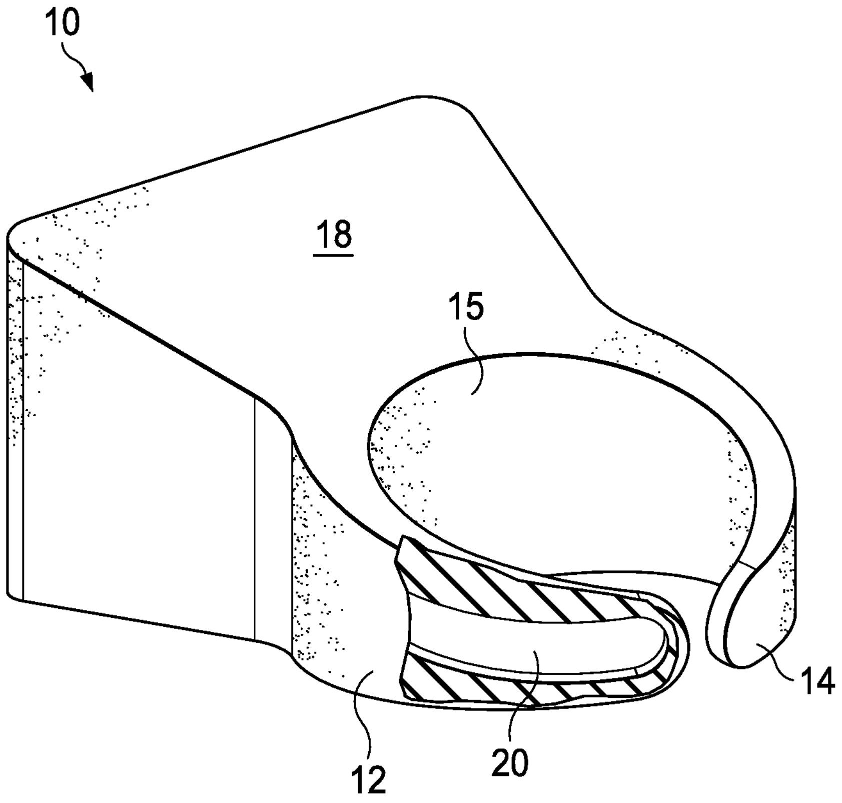
FIG. 9 is a partial cut-away perspective view of a neck collar according to one embodiment.

Turning now to FIG. 9, there is shown a partial cutaway view of a neck collar 10, showing the elastically deformable spring member 20 being disposed within the neck collar 10. In an embodiment the elastically deformable spring member 20 is completely enclosed in neck collar 10 and is not visible or noticeable to the user, except in its effect as a spring member to allow collar straps 12 and 14 to separate, i.e., enlarge gap G enough to go around the neck of a user, and then return to a relaxed position.

Figure 10:
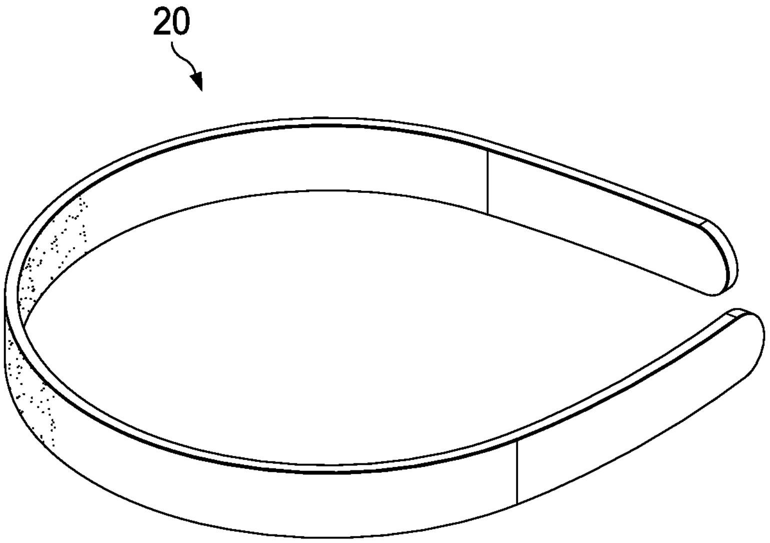
FIG. 10 is a perspective view of an elastically deformable spring member according to one embodiment.

Referring now to FIG. 10, there is shown a representative elastically deformable spring member 20. Elastically deformable spring member 20 can be made of plastic, and can be made of steel, such as spring steel.

Neck collar 10 can be made by a foam injection process. In an embodiment the foam is an open foam. In an embodiment, the foam is a closed foam. In an embodiment, the elastically deformable spring member 20 is positioned in a mold in a relaxed state and a foaming polymer is injected in the mold and around the elastically deformable spring member 20, such that the final product is a unitary product of relatively soft foam having generally immovably positioned therein a elastically deformable spring member 20, as described above.

The neck collar 10 will take the shape of the mold used in the foam injection process, and this shape can be the generally wedge-shape, as seen in the side view of FIG. 6, or generally cylindrically shaped as shown in FIGS. 7 and 8. However, other shapes of the neck collar 10 are envisioned and can be made, as long as the neck collar shape when in use can sufficiently support the chin and head of a user in a generally erect position.

In an embodiment, the neck collar 10 is made entirely of foamed polymer from a foam injection mold process with the elastically deformable spring member 20 embedded therein. In an embodiment the foam injection process involves the use of a foaming agent, such as nitrogen gas, mixed with a melted polymer and injected into a mold. The process of foam injection molding can result in a neck pillow 10 having the shape of the mold, and having a relatively dense outer skin, the dense outer skin being a durable surface of the final product. That is, upon completion of the foam injection molding process, which can involve colorants to produce a neck pillow 10 of a desired color, the neck pillow 10, when removed from the mold, can be in its final, in-use, condition.

The molding process for making the neck collar 10 can be achieved in an aluminum mold which can be heated to a high temperature. The high temperature of the mold can be sufficient to melt the resin so completely that the foam cell size is reduced, creating a relatively dense version of the foam on the surface of the neck collar 10. In an embodiment such a product is referred to integral self-skinned foam. The outer skin forms the outer surface of neck collar 10, and can provide protection against scratch and abrasion, as well as being a relatively easily cleanable surface for cleaning food and liquid/fluid spills such as drooling. Moreover, the outer skin can render, in effect, the neck collar 10 a closed foam pillow in the sense that the outer periphery of neck collar 10 is closed, i.e., any air or gas in the inner interstices of foam neck collar 10 is substantially blocked from escape through the outer skin.

In an embodiment, the neck pillow 10 can be covered with a covering, such as a flexible fabric casing that can be form fitted and secured to the neck collar 10.

In an embodiment, a flexible nonwoven material which is intended to be disposable can be cut to shape and applied on the top surface 18 and/or bottom surface 16 of neck pillow 10. The flexible nonwoven material can be discarded as desired, for example after use. Examples of nonwoven materials applied to neck pillow 10 include spunbond polypropylene having a basis weight from about 10 to about 100 grams per square meter. The nonwoven material can be “self-clinging” to the surface of the neck collar 10. The nonwoven material can also have connection parts, such as hook and loop fasteners, or removable adhesive, to attach to the neck collar 10. The nonwoven material can also be printed, such as by Inkjet or flexographic printing, to have various designs.

In an embodiment the neck collar 10 can have a weight ranging from about 1 ounce to about 10 ounces, about 2 ounces to about 5 ounces. In an embodiment, the neck collar 10 can weigh about 2.4 ounces.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed is:

1. A non-restraining collar, the non-restraining collar comprising:

a. a unitary pillow, the unitary pillow having:

i. a collar body;

ii. a first collar strap extending from the collar body and terminating at a first end; and iii. a second collar strap extending from the collar body and terminating at a second end, wherein the second collar strap is positioned opposite the first collar strap;

wherein the first end of the first collar strap is spaced apart from the second end of the second collar strap by a space having a first distance in a relaxed state, and wherein the collar body projects outwardly from the first collar strap and the second collar strap such that a portion of a user may be supported thereon;

b. an elastically deformable spring member positioned within the unitary pillow, the elastically deformable spring member having a first spring member portion extending into the first collar strap and a second spring member portion extending into the second collar strap; wherein the elastically deformable spring member is elastically deformable to an open position such that the space has a second distance greater than the first distance.

2. The non-restraining collar of claim 1, wherein the unitary pillow includes an integral skin.

3. The non-restraining collar of claim 1, wherein the first distance is about zero inches.

4. The non-restraining collar of claim 1, wherein the second distance is about five inches.

5. The non-restraining collar of claim 1, wherein the elastically deformable spring member is made of plastic or metal, and a material of the unitary pillow is polyurethane.

6. The non-restraining collar of claim 1, wherein the non-restraining collar does not comprise a fastening member.

7. The non-restraining collar of claim 1, wherein the first spring member portion and the second spring member portion are separate elements not directly coupled to one another.

8. A non-restraining collar for ease of placement and removal, the non-restraining collar comprising:

a. a unitary pillow, the unitary pillow having:

i. a collar body;

ii. a first collar strap extending from the collar body and terminating at a first end; and iii. a second collar strap extending from the collar body and terminating at a second end, wherein the second collar strap is positioned opposite the first collar strap;

wherein the first end of the first collar strap is spaced apart from the second end of the second collar strap by a space having a first distance in a relaxed state, and wherein the collar body projects outwardly from the first collar strap and the second collar strap such that a portion of a user may be supported thereon;

b. an elastically deformable spring member positioned within the unitary pillow, the elastically deformable spring member having a first spring member portion extending into the first collar strap and a second spring member portion extending into the second collar strap; wherein the elastically deformable spring member is elastically deformable to an open position such that the space has a second distance greater than the first distance; and c. the elastically deformable spring member resisting being deformed to the open position in the absence of fastening members on the unitary pillow.

9. The non-restraining collar of claim 8, wherein the unitary pillow further comprises an integral skin.

10. The non-restraining collar of claim 8, wherein the first collar strap and the second collar strap are disposed in a plane and are symmetric about the plane.

11. The non-restraining collar of claim 8, wherein the second distance is about five inches.

12. The non-restraining collar of claim 8, wherein the elastically deformable spring member is made of plastic or metal, and a material of the unitary pillow is polyurethane.

13. The non-restraining collar of claim 8, wherein the non-restraining collar does not comprise a fastening member.

14. A method for supporting a portion of a person in need of support, the method comprising the steps of:

providing a non-restraining collar, the non-restraining collar comprising, a. a unitary pillow, the unitary pillow having:

i. a collar body;

ii. a first collar strap extending from the collar body and terminating at a first end; and iii. a second collar strap extending from the collar body and terminating at a second end, wherein the second collar strap is positioned opposite the first collar strap;

wherein the first end of the first collar strap is spaced apart from the second end of the second collar strap by a space having a first distance in a relaxed state, and wherein the collar body projects outwardly from the first collar strap and the second collar strap such that the portion of the person may be supported thereon;

b. an elastically deformable spring member positioned within the unitary pillow, the elastically deformable spring member having a first spring member portion extending into the first collar strap and a second spring member portion extending into the second collar strap; wherein the elastically deformable spring member is elastically deformable to an open position such that the space has a second distance greater than the first distance; and c. the elastically deformable spring member resisting being deformed to the open position in the absence of fastening members on the unitary pillow;

urging the first end and the second end to the open position at the second distance;

placing the non-restraining collar around the portion of the person; and allowing the first end and the second end to return to the first distance.

15. The method of claim 14, wherein the unitary pillow comprises in integral skin.

16. The method of claim 14, wherein the first spring member portion and the second spring member portion are separate elements that are not directly coupled to one another.

17. The method of claim 14, wherein the first distance is about zero inches.

18. The method of claim 14, wherein the second distance is about five inches.

19. The method of claim 14, wherein the elastically deformable spring member is made of plastic or metal, and a material of the unitary pillow is polyurethane.

20. The method of claim 14, wherein the non-restraining collar does not comprise a fastening member.

* * * * *